US008696679B2

(12) United States Patent
Shadduck et al.

(10) Patent No.: US 8,696,679 B2
(45) Date of Patent: Apr. 15, 2014

(54) BONE TREATMENT SYSTEMS AND METHODS

(75) Inventors: John H. Shadduck, Tiburon, CA (US); Csaba Truckai, Saratoga, CA (US)

(73) Assignee: Dfine, Inc., San Jose, CA (US)

( * ) Notice: Subject to any disclaimer, the term of this patent is extended or adjusted under 35 U.S.C. 154(b) by 1112 days.

(21) Appl. No.: 11/953,800

(22) Filed: Dec. 10, 2007

(65) Prior Publication Data

US 2008/0154273 A1 Jun. 26, 2008

Related U.S. Application Data

(60) Provisional application No. 60/873,590, filed on Dec. 8, 2006.

(51) Int. Cl.
*A61F 2/00* (2006.01)
(52) U.S. Cl.
USPC ............................................................. 606/94
(58) Field of Classification Search
USPC ...................... 623/17.11–17.16, 23.61–23.62;
606/92–94; 604/23–24, 113, 131,
604/144–147, 150, 82–92; 523/113–116;
433/32, 80, 89–90; 222/146.1–146.4;
239/8–9
See application file for complete search history.

(56) References Cited

U.S. PATENT DOCUMENTS

| 3,349,840 A | 10/1967 | Tope et al. |
| 4,265,618 A | 5/1981 | Herskovitz et al. |
| 4,280,233 A | 7/1981 | Raab |
| 4,294,251 A | 10/1981 | Greenwald et al. |
| 4,338,925 A | 7/1982 | Miller |
| 4,377,168 A | 3/1983 | Rzasa et al. |
| 4,735,625 A | 4/1988 | Davidson |
| 4,772,287 A | 9/1988 | Ray et al. |
| 4,849,223 A | 7/1989 | Pratt et al. |

(Continued)

FOREIGN PATENT DOCUMENTS

| WO | WO 02/058592 | 8/2002 |
| WO | WO 02/064062 | 8/2002 |

(Continued)

OTHER PUBLICATIONS

International Search Report PCT/US2005/043984, mailed Jun. 20, 2006.

(Continued)

*Primary Examiner* — Matthew Lawson
(74) *Attorney, Agent, or Firm* — Knobbe, Martens, Olson & Bear LLP

(57) ABSTRACT

The present invention relates in certain embodiments to methods, systems, and devices for treating vertebral compression fractures. In one embodiment, a bone cement injector is advanced into bone and injects a bone cement flow through the injector and a vapor flow from at least one vapor outlet in the injector. In another embodiment, the bone treatment system comprises an elongated member having a flow passageway, a bone fill material source, and a vapor source coupleable to the flow passageway. Still another embodiment describes a vapor injection device having an elongated member with a flow passageway, the elongated member configured for insertion into a bone and for delivering a bone fill material through the flow passageway, and having at least one vapor channel in communication with the flow passageway to deliver a vapor into the flow passageway to heat a bone fill material flow.

25 Claims, 9 Drawing Sheets

(56) References Cited

U.S. PATENT DOCUMENTS

| | | | |
|---|---|---|---|
| 4,959,104 A | 9/1990 | Lino et al. | |
| 4,963,151 A | 10/1990 | Ducheyne et al. | |
| 4,969,888 A | 11/1990 | Scholten et al. | |
| 4,969,906 A | 11/1990 | Kronman | |
| 5,037,437 A | 8/1991 | Matsen, III | |
| 5,051,482 A | 9/1991 | Tepic | |
| 5,108,404 A | 4/1992 | Scholten et al. | |
| 5,130,950 A | 7/1992 | Orban et al. | |
| 5,145,250 A | 9/1992 | Planck et al. | |
| 5,336,700 A * | 8/1994 | Murray | 523/116 |
| 5,431,654 A | 7/1995 | Nic | |
| 5,514,135 A | 5/1996 | Earle | |
| 5,542,928 A | 8/1996 | Evans et al. | |
| 5,574,075 A | 11/1996 | Draenert | |
| 5,679,299 A | 10/1997 | Gilbert et al. | |
| 5,693,099 A | 12/1997 | Harle | |
| 5,788,711 A | 8/1998 | Lehner et al. | |
| 5,814,681 A | 9/1998 | Hino et al. | |
| 5,954,716 A | 9/1999 | Sharkey et al. | |
| 6,048,346 A | 4/2000 | Reiley | |
| 6,075,067 A | 6/2000 | Lidgren | |
| 6,122,549 A | 9/2000 | Sharkey et al. | |
| 6,171,312 B1 | 1/2001 | Beaty | |
| 6,210,404 B1 * | 4/2001 | Shadduck | 606/34 |
| 6,231,615 B1 | 5/2001 | Preissman | |
| 6,235,043 B1 | 5/2001 | Reiley et al. | |
| 6,236,020 B1 | 5/2001 | Friedman | |
| 6,241,734 B1 | 6/2001 | Scribner | |
| 6,248,110 B1 | 6/2001 | Reiley et al. | |
| 6,261,289 B1 | 7/2001 | Levy | |
| 6,264,659 B1 | 7/2001 | Ross et al. | |
| 6,280,456 B1 | 8/2001 | Scribner | |
| 6,309,420 B1 | 10/2001 | Preissman | |
| 6,312,254 B1 * | 11/2001 | Friedman | 433/32 |
| 6,316,885 B1 | 11/2001 | Collins et al. | |
| 6,319,255 B1 | 11/2001 | Grundei et al. | |
| 6,332,894 B1 | 12/2001 | Stalcup et al. | |
| 6,358,254 B1 | 3/2002 | Anderson | |
| 6,395,007 B1 | 5/2002 | Bhatnagar et al. | |
| 6,425,923 B1 | 7/2002 | Stalcup et al. | |
| 6,436,143 B1 * | 8/2002 | Ross et al. | 623/17.16 |
| 6,439,439 B1 | 8/2002 | Rickard | |
| 6,443,988 B2 | 9/2002 | Felt et al. | |
| 6,447,514 B1 | 9/2002 | Stalcup et al. | |
| 6,458,127 B1 | 10/2002 | Truckai | |
| 6,458,375 B1 | 10/2002 | Gertzman et al. | |
| 6,458,812 B1 | 10/2002 | McKittrick et al. | |
| 6,485,436 B1 * | 11/2002 | Truckai et al. | 600/564 |
| 6,508,816 B2 * | 1/2003 | Shadduck | 606/34 |
| 6,524,102 B2 | 2/2003 | Davis | |
| 6,610,079 B1 | 8/2003 | Li et al. | |
| 6,613,054 B2 | 9/2003 | Scribner et al. | |
| 6,632,235 B2 | 10/2003 | Weikel et al. | |
| 6,676,664 B1 | 1/2004 | Al-Assir | |
| 6,706,069 B2 | 3/2004 | Berger | |
| 6,709,149 B1 | 3/2004 | Tepic | |
| 6,712,852 B1 | 3/2004 | Chung et al. | |
| 6,716,216 B1 | 4/2004 | Boucher | |
| 6,723,095 B2 | 4/2004 | Hammerslag | |
| 6,726,691 B2 * | 4/2004 | Osorio et al. | 606/94 |
| 6,726,991 B2 | 4/2004 | Kaeding et al. | |
| 6,740,093 B2 | 5/2004 | Hochschuler et al. | |
| 6,767,936 B2 | 7/2004 | Walz et al. | |
| 6,783,515 B1 | 8/2004 | Miller | |
| 6,814,736 B2 | 11/2004 | Reiley | |
| 6,872,403 B2 | 3/2005 | Pienkowski et al. | |
| 6,890,332 B2 * | 5/2005 | Truckai et al. | 606/41 |
| 6,899,713 B2 | 5/2005 | Shaolian et al. | |
| 6,911,028 B2 | 6/2005 | Shadduck | |
| 6,929,640 B1 | 8/2005 | Underwood | |
| 6,958,061 B2 | 10/2005 | Truckai | |
| 6,964,667 B2 | 11/2005 | Shaolian et al. | |
| 6,979,352 B2 * | 12/2005 | Reynolds | 623/17.11 |
| 6,981,981 B2 | 1/2006 | Reiley | |
| 6,985,061 B2 | 1/2006 | Hafskjold et al. | |
| 7,008,433 B2 * | 3/2006 | Voellmicke et al. | 606/93 |
| 7,044,954 B2 | 5/2006 | Reiley | |
| 7,081,125 B2 | 7/2006 | Edwards et al. | |
| 7,091,460 B2 | 8/2006 | Kinzer | |
| 7,108,696 B2 | 9/2006 | Daniel et al. | |
| 7,112,205 B2 | 9/2006 | Carrlson | |
| 7,115,163 B2 | 10/2006 | Zimmermann | |
| 7,153,306 B2 | 12/2006 | Ralph | |
| 7,153,307 B2 | 12/2006 | Scribner | |
| 7,160,020 B2 | 1/2007 | Sand | |
| 7,273,523 B2 | 9/2007 | Wenz | |
| 7,306,598 B2 | 12/2007 | Truckai et al. | |
| 7,335,195 B2 * | 2/2008 | Mehier | 606/27 |
| 7,341,569 B2 * | 3/2008 | Soltani et al. | 604/22 |
| 7,357,802 B2 * | 4/2008 | Palanker et al. | 606/45 |
| 7,559,932 B2 | 7/2009 | Truckai et al. | |
| 7,632,294 B2 | 12/2009 | Milbocker et al. | |
| 7,662,133 B2 | 2/2010 | Scarborough et al. | |
| 7,674,259 B2 | 3/2010 | Shadduck | |
| 2001/0011190 A1 | 8/2001 | Park | |
| 2001/0012968 A1 | 8/2001 | Preissman | |
| 2002/0026195 A1 | 2/2002 | Layne et al. | |
| 2002/0032447 A1 | 3/2002 | Weikel et al. | |
| 2002/0068974 A1 | 6/2002 | Kuslich et al. | |
| 2002/0082608 A1 | 6/2002 | Reiley et al. | |
| 2002/0099385 A1 | 7/2002 | Ralph et al. | |
| 2002/0147497 A1 | 10/2002 | Belef et al. | |
| 2002/0156483 A1 | 10/2002 | Voellmicke et al. | |
| 2002/0161373 A1 | 10/2002 | Osorio et al. | |
| 2002/0165582 A1 * | 11/2002 | Porter | 606/213 |
| 2002/0183758 A1 | 12/2002 | Middleton et al. | |
| 2003/0012080 A1 | 1/2003 | Coffeen et al. | |
| 2003/0032733 A1 | 2/2003 | Fisher et al. | |
| 2003/0032929 A1 | 2/2003 | McGuckin | |
| 2003/0130373 A1 | 7/2003 | Walz et al. | |
| 2003/0130664 A1 | 7/2003 | Boucher et al. | |
| 2003/0130738 A1 | 7/2003 | Hovda et al. | |
| 2003/0171748 A1 | 9/2003 | Truckai et al. | |
| 2003/0208192 A1 | 11/2003 | Truckai et al. | |
| 2003/0220648 A1 | 11/2003 | Osorio et al. | |
| 2003/0233096 A1 | 12/2003 | Osorio et al. | |
| 2004/0006347 A1 | 1/2004 | Sproul | |
| 2004/0024410 A1 | 2/2004 | Olson, Jr. et al. | |
| 2004/0059328 A1 * | 3/2004 | Daniel et al. | 606/41 |
| 2004/0068306 A1 * | 4/2004 | Shadduck | 607/96 |
| 2004/0073308 A1 | 4/2004 | Kuslich et al. | |
| 2004/0083002 A1 | 4/2004 | Belef et al. | |
| 2004/0091366 A1 * | 5/2004 | Chung et al. | 417/151 |
| 2004/0092948 A1 | 5/2004 | Stevens et al. | |
| 2004/0102845 A1 | 5/2004 | Reynolds | |
| 2004/0110285 A1 | 6/2004 | Lendlein | |
| 2004/0138655 A1 * | 7/2004 | McClurken et al. | 606/34 |
| 2004/0138748 A1 | 7/2004 | Boyer, II et al. | |
| 2004/0167561 A1 | 8/2004 | Boucher et al. | |
| 2004/0172132 A1 | 9/2004 | Ginn | |
| 2004/0186576 A1 | 9/2004 | Biscup et al. | |
| 2004/0193171 A1 * | 9/2004 | DiMauro et al. | 606/92 |
| 2004/0199226 A1 * | 10/2004 | Shadduck | 607/96 |
| 2004/0225296 A1 | 11/2004 | Reiss et al. | |
| 2004/0225926 A1 | 11/2004 | Scales et al. | |
| 2004/0228898 A1 * | 11/2004 | Ross et al. | 424/423 |
| 2004/0267271 A9 | 12/2004 | Scribner et al. | |
| 2004/0267272 A1 | 12/2004 | Henniges | |
| 2005/0010231 A1 | 1/2005 | Myers | |
| 2005/0015148 A1 | 1/2005 | Jansen et al. | |
| 2005/0059979 A1 | 3/2005 | Yetkinler et al. | |
| 2005/0070913 A1 * | 3/2005 | Milbocker et al. | 606/92 |
| 2005/0113843 A1 | 5/2005 | Arramon | |
| 2005/0119650 A1 | 6/2005 | Sanders et al. | |
| 2005/0180806 A1 | 8/2005 | Green et al. | |
| 2005/0199386 A1 * | 9/2005 | Kinzer | 166/248 |
| 2005/0199650 A1 * | 9/2005 | Nyhof et al. | 222/105 |
| 2005/0209595 A1 | 9/2005 | Karmon | |
| 2005/0222681 A1 | 10/2005 | Richley et al. | |
| 2005/0245938 A1 * | 11/2005 | Kochan | 606/92 |
| 2005/0251149 A1 * | 11/2005 | Wenz | 606/94 |
| 2005/0282117 A1 * | 12/2005 | Aravena et al. | 433/224 |
| 2006/0052743 A1 | 3/2006 | Reynolds | |
| 2006/0052794 A1 | 3/2006 | McGill et al. | |

(56) References Cited

U.S. PATENT DOCUMENTS

| | | | |
|---|---|---|---|
| 2006/0064145 A1* | 3/2006 | Podhajsky | 607/96 |
| 2006/0074433 A1* | 4/2006 | McGill et al. | 606/92 |
| 2006/0079905 A1 | 4/2006 | Beyar et al. | |
| 2006/0095138 A1 | 5/2006 | Truckai et al. | |
| 2006/0100635 A1 | 5/2006 | Reiley et al. | |
| 2006/0100706 A1 | 5/2006 | Shadduck et al. | |
| 2006/0106459 A1* | 5/2006 | Truckai et al. | 623/17.11 |
| 2006/0122614 A1 | 6/2006 | Truckai et al. | |
| 2006/0122621 A1 | 6/2006 | Truckai et al. | |
| 2006/0122622 A1* | 6/2006 | Truckai et al. | 606/94 |
| 2006/0122623 A1 | 6/2006 | Truckai et al. | |
| 2006/0122624 A1* | 6/2006 | Truckai et al. | 606/94 |
| 2006/0122625 A1 | 6/2006 | Truckai et al. | |
| 2006/0135955 A1* | 6/2006 | Shadduck | 606/27 |
| 2006/0150862 A1 | 7/2006 | Zhao et al. | |
| 2006/0224154 A1 | 10/2006 | Shadduck | |
| 2006/0229625 A1 | 10/2006 | Truckai et al. | |
| 2006/0229628 A1* | 10/2006 | Truckai et al. | 606/90 |
| 2006/0264965 A1 | 11/2006 | Shadduck et al. | |
| 2007/0022912 A1 | 2/2007 | Zimmermann | |
| 2007/0027230 A1* | 2/2007 | Beyar et al. | 523/117 |
| 2007/0032567 A1 | 2/2007 | Beyar et al. | |
| 2007/0032785 A1* | 2/2007 | Diederich et al. | 606/27 |
| 2007/0055277 A1* | 3/2007 | Osorio et al. | 606/92 |
| 2007/0098801 A1* | 5/2007 | Verreck et al. | 424/489 |
| 2007/0112299 A1 | 5/2007 | Smit et al. | |
| 2007/0118144 A1 | 5/2007 | Truckai et al. | |
| 2007/0162043 A1 | 7/2007 | Truckai et al. | |
| 2007/0185231 A1 | 8/2007 | Liu et al. | |
| 2007/0191858 A1 | 8/2007 | Truckai et al. | |
| 2007/0191964 A1 | 8/2007 | Preissman | |
| 2007/0233148 A1 | 10/2007 | Truckai et al. | |
| 2007/0233249 A1 | 10/2007 | Shadduck | |
| 2007/0233250 A1 | 10/2007 | Shadduck | |
| 2007/0260250 A1* | 11/2007 | Wisnewski et al. | 606/73 |
| 2008/0103505 A1 | 5/2008 | Fransen | |
| 2008/0132826 A1 | 6/2008 | Shadduck | |
| 2008/0195112 A1 | 8/2008 | Liu et al. | |
| 2008/0208196 A1 | 8/2008 | Daum | |
| 2008/0319445 A9* | 12/2008 | McGill et al. | 606/92 |
| 2009/0024161 A1 | 1/2009 | Bonutti et al. | |

FOREIGN PATENT DOCUMENTS

| | | |
|---|---|---|
| WO | WO 02/087416 | 11/2002 |
| WO | WO 2004/075954 | 9/2004 |
| WO | WO 2006/031490 | 3/2006 |
| WO | WO 2006/062916 | 6/2006 |
| WO | WO 2006/062939 | 6/2006 |
| WO | WO 2006/130491 | 12/2006 |
| WO | WO 2007/028120 | 3/2007 |
| WO | WO 2008/097855 | 8/2008 |
| WO | WO 2009/108893 | 9/2009 |

OTHER PUBLICATIONS

International Search Report PCT/US2005/044055, mailed May 31, 2006.
U.S. Appl. No. 11/469,752, filed Sep. 1, 2006, Truckai et al.
U.S. Appl. No. 11/469,769, filed Sep. 1, 2006, Truckai et al.
International Search Report for PCT Application No. PCT/US2006/034409 mailed Apr. 16, 2007.
Office Action in U.S. Appl. No. 11/148,973 mailed Jun. 29, 2007.
Office Action in U.S. Appl. No. 11/148,973 mailed Feb. 28, 2008.
Office Action in U.S. Appl. No. 11/165,045 mailed Mar. 26, 2008.
Office Action in U.S. Appl. No. 11/165,651 mailed Sep. 21, 2007.
Office Action in U.S. Appl. No. 11/165,651 mailed Mar. 24, 2008.
Office Action in U.S. Appl. No. 11/165,651, mailed Sep. 22, 2008.
Office Action in U.S. Appl. No. 11/165,652 mailed Oct. 3, 2007.
Office Action in U.S. Appl. No. 11/165,652 mailed Mar. 20, 2008.
Office Action in U.S. App. No. 11/165,652, mailed Sep. 19, 2008.
Office Action in U.S. Appl. No. 11/196,089 mailed Jan. 3, 2008.
Office Action in U.S. Appl. No. 11/196,089, mailed Sep. 19, 2008.
Office Action in U.S. Appl. No. 11/208,448 mailed Nov. 30, 2007.
Office Action in U.S. Appl. No. 11/208,448, mailed Sep. 8, 2008.
Office Action in U.S. Appl. No. 11/209,035 mailed Jan. 3, 2008.
Office Action in U.S. Appl. No. 11/209,035 mailed Sep. 18, 2008.
Allowed Claims in U.S. Appl. No. 11/165,651.
Carrodeguas, et al., "Injectable Acrylic Bone Cements for Vertebroplasty with Improved Properties", Journal of Biomedical Materials Research, XP002312783, vol. 68, No. 1, Jan. 15, 2004, pp. 94-104.
Furderer S, Anders M, Schwindling B, Salick M, Duber C, Wenda K, Urban R, Gluck M, Eysel P., "Vertebral body stenting. A method for repositioning and augmenting vertebral compression fractures", Orthopade. Apr. 2002; 31(4):356-61, Abstract.
Pending Claims in the Amendment in response to non-final Office Action mailed Sep. 19, 2008 in U.S. Appl. No. 11/165,652.
Pending Claims in the Amendment in response to non-final Office Action mailed Sep. 22, 2008 in U.S. Appl. No. 11/165,651.
Office Action in U.S. Appl. No. 11/196,045, mailed Oct. 3, 2008.
Office Action in U.S. Appl. No. 11/196,045, mailed Apr. 3, 2009.
Office Action in U.S. Appl. No. 11/196,045, mailed Jan. 7, 2010.
Pending Claims in the Amendment in response to non-final Office Action mailed Oct. 3, 2008 in U.S. Appl. No. 11/196,045.
Office Action in U.S. Appl. No. 11/196,089, mailed May 8, 2009.
Office Action in U.S. Appl. No. 11/196,089, mailed Dec. 28, 2009.
Office Action in U.S. Appl. No. 11/208,448, mailed Apr. 3, 2009.
Office Action in U.S. Appl. No. 11/208,448, mailed Dec. 29, 2009.
Pending Claims in the Amendment in response to non-final Office Action mailed Sep. 8, 2008 in U.S. Appl. No. 11/208,448.
Office Action in U.S. Appl. No. 11/209,035, mailed May 20, 2009.
Exam Report for EPO App. 05 848 386.8 dated Sep. 18, 2009 in 5 pgs.
Office Action in U.S. Appl. No. 11/148,973, mailed Apr. 16, 2009.
Office Action in U.S. Appl. No. 11/148,973, mailed Sep. 26, 2009.
Office Action in U.S. Appl. No. 11/148,973, mailed Nov. 27, 2009.
Office Action in U.S. Appl. No. 11/469,769, mailed Dec. 11, 2008.
Office Action in U.S. Appl. No. 11/469,769, mailed Oct. 2, 2009.

* cited by examiner

BONE TREATMENT SYSTEMS AND METHODS

CROSS-REFERENCE TO RELATED APPLICATIONS

This application claims the benefit of U.S. Provisional Patent Application No. 60/873,590, filed on Dec. 8, 2006, the entire contents of which are hereby incorporated by reference and should be considered a part of this specification. The present application is related to the following U.S. Patent Applications: App. Ser. No. 11/469,764 filed Sept. 1, 2006; App. Ser. No. 11/165,652 filed Jun. 24, 2005; App. Ser. No. 60/726,152 filed Oct. 13, 2005 titled Bone Treatment Systems and Methods; and App. Ser. No. 11/209,035 filed Aug. 22, 2005. The entire contents of all of the above applications are hereby incorporated by reference and should be considered a part of this specification.

BACKGROUND OF THE INVENTION

1. Field of the Invention

The present invention relates in certain embodiments to systems for treating vertebral compression fractures. In some embodiments, systems and methods for treating bone are disclosed that include delivering a bone fill material into bone, and heating the bone fill material using a vapor source to alter a property of the bone fill material prior to its introduction into bone. In one embodiment, a tubular sleeve is configured as a port that is screwed into the cortical bone of a pedicle to allow instrument exchange through the port into the interior of the vertebra. Another embodiment includes a member with an electrosurgical surface or a sensing electrode surface in a member that includes an insulative diamond-like surface coating.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See "Anatomical and Pathological Considerations in Percutaneous Vertebroplasty and Kyphoplasty: A Reappraisal of the Vertebral Venous System", Groen, R. et al, Spine Vol. 29, No. 13, pp 1465-1471 2004. Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al, "The Analysis of Polymethylmethacrylate Leakage after Vertebroplasty for Vertebral Body Compression Fractures", Jour. of Korean Neurosurg. Soc. Vol. 35, No. 5 (May 2004) pp. 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol. 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al, "Asymptomatic diffuse pulmonary embolism caused by acrylic cement: an unusual complication of percutaneous vertebroplasty", Ann. Rheum. Dis. 2003; 62:85-86. The vapors from PMMA preparation and injection also are cause for concern. See Kirby, B, et al., "Acute bronchospasm due to exposure to polymethylmethacrylate vapors during percutaneous vertebroplasty", Am. J. Roentgenol. 2003; 180:543-544.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon applies also compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which crushes and compacts cancellous bone. Expansion of the balloon under high pressures close to cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

There is a general need to provide bone cements and methods for use in treatment of vertebral compression fractures that provide a greater degree of control over introduction of cement and that provide better outcomes. The present invention meets this need and provides several other advantages in a novel and non-obvious manner.

SUMMARY OF THE INVENTION

Certain embodiments of the present invention are directed to systems for treating vertebral compression fractures. In some embodiments, systems and methods for treating bone are disclosed that include delivering a bone fill material into bone, and heating the bone fill material using a vapor source to alter a property of the bone fill material prior to its introduction into bone. In one embodiment, a tubular sleeve is configured as a port that is screwed into the cortical bone of a pedicle to allow instrument exchange through the port into the interior of the vertebra. Another embodiment includes a member with an electrosurgical surface or a sensing electrode surface in a member that includes an insulative diamond-like surface coating.

Certain embodiments of the invention provide vertebroplasty systems and methods for sensing retrograde bone cement flows that can migrate along a fractured path toward a pedicle and risk leakage into the spinal canal. The physician can be alerted instantaneously of cement migration in a direction that may impinge on nerves or the spinal cord. Other embodiments include integrated sensing systems and energy delivery systems for applying energy to tissue and/or to bone cement that migrates in a retrograde direction wherein the energy polymerizes the cement and/or coagulates tissue to create a dam to prevent further cement migration. In another embodiment, the systems provide a cooling system for cooling bone cement in a remote container or injection cannula for controlling and extending the working time of bone cement. In another embodiment, the bone cement injection system includes a thermal energy emitter for warming bone cement within an injector or for applying sufficient energy to accelerate polymerization and thereby increase the viscosity of the bone cement.

In one embodiment, a computer controller is provided to controls cement inflow parameters from a hydraulic source, the sensing system and energy delivery parameters for selectively heating tissue or polymerizing cement at both the interior and exterior of the injector to thereby control all parameters of cement injection to reduce workload on the physician.

In another embodiment, a lubricous surface layer is provided in the flow passageway of the bone cement injector to inhibit sticking of the bone cement to the wall of the flow channel of the introducer, particularly when heating the cement.

In accordance with one embodiment, a method for treating bone is provided, the method comprises advancing a bone cement injector into bone, providing a bone cement flow through the injector into the bone, and introducing vapor into the bone cement flow from at least one vapor outlet in the injector.

In accordance with another embodiment, a bone treatment system is provided. The bone treatment system comprises an elongated injector having a flow passageway extending therethrough, a source of bone fill material coupleable to the flow passageway and configured to deliver a flow of bone fill material through the flow passageway, and a vapor source operatively coupleable to at least one channel in the injector that is in communication with the flow passageway for injecting vapor into the flow passageway to heat the bone fill material in the passageway.

In accordance with another embodiment, a device for treating a bone is provided. The device comprises an elongated member having a flow passageway extending therethrough to a distal outlet opening, the elongated member configured for insertion into a bone and for delivering a bone fill material through the flow passageway. The elongated member further comprises at least one channel in communication with the flow passageway via a plurality of openings, the at least one channel configured to deliver a vapor therethrough into the flow passageway to heat a bone fill material flow.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

DETAILED DESCRIPTION OF THE PREFERRED EMBODIMENTS

Figure 1:
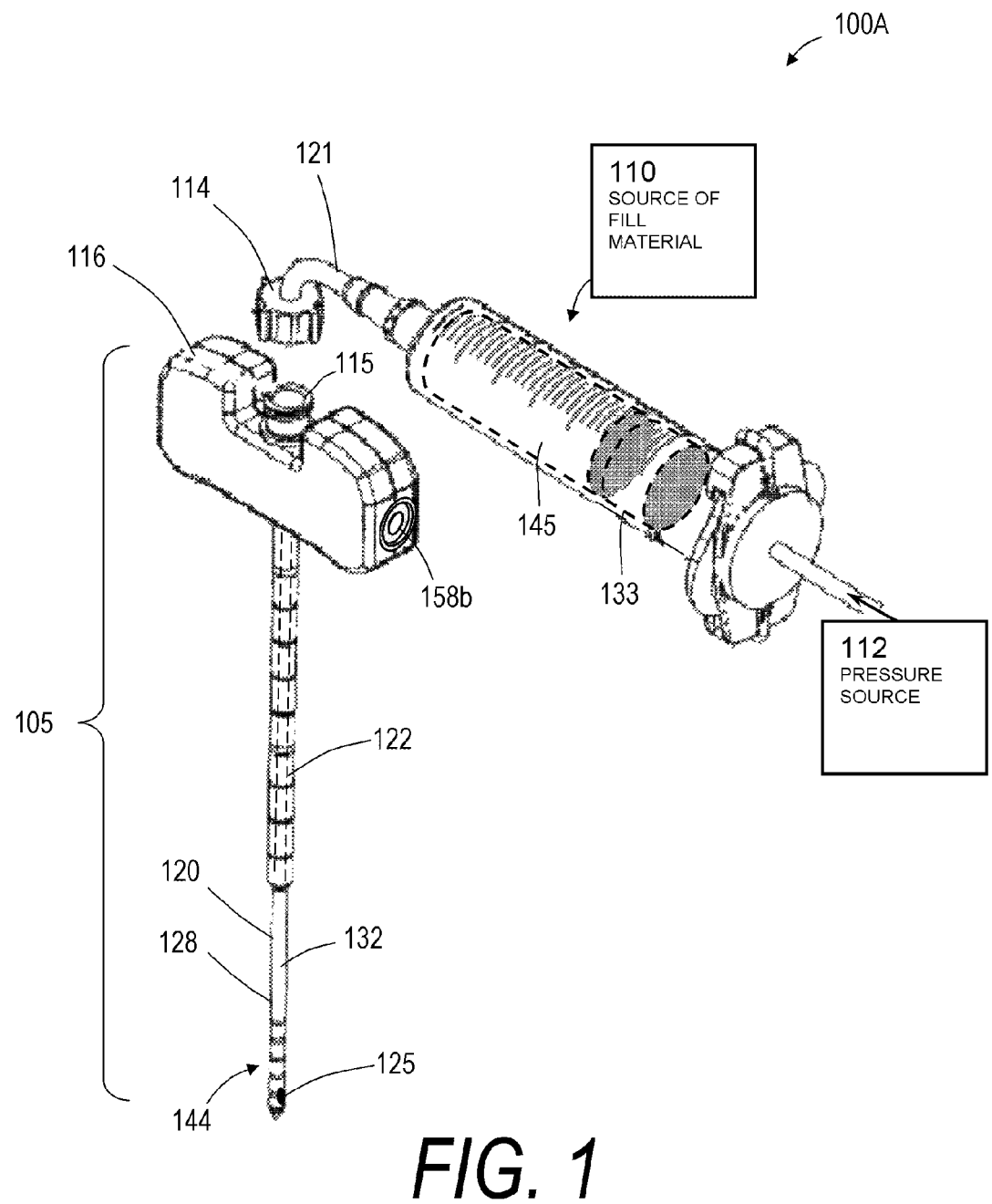
FIG. 1 is a schematic perspective view of one embodiment of a bone cement injection system and sensing system.
Figure 2:
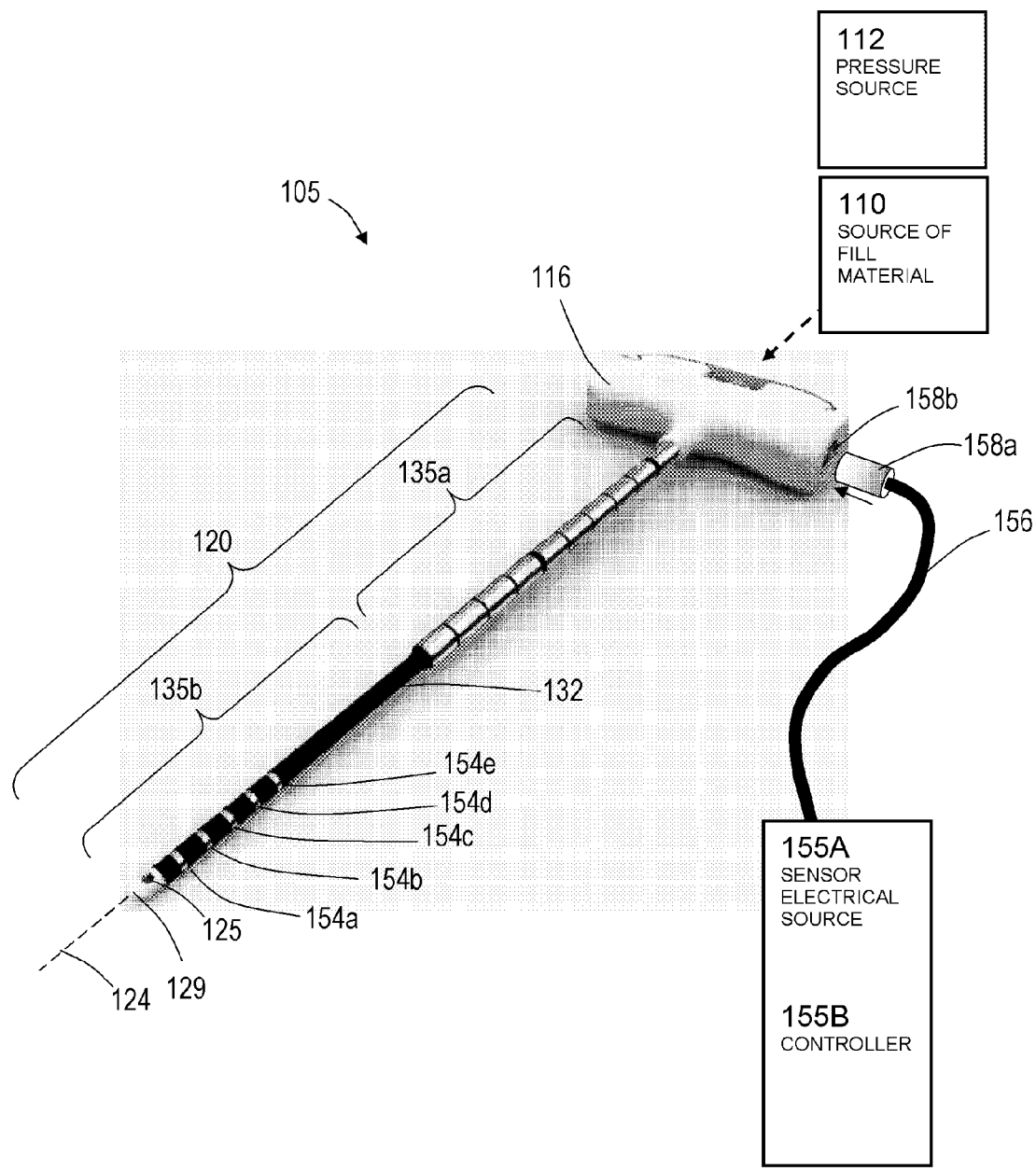
FIG. 2 is another schematic view of the bone cement injector of FIG. 1.

For the purpose of understanding the principles of the invention, reference will now be made to the embodiments illustrated in the drawings and accompanying text that describe different embodiments of the invention. Referring to FIGS. 1-2, one embodiment of a bone fill introducer or injector system 100A is shown that can be used for treatment of the spine in a vertebroplasty procedure. The system 100A includes a bone cement injector 105 that is coupled to source 110 of a bone fill material wherein the injection of the fill material is carried out by a pressure mechanism or source 112 operatively coupled to the source 110 of bone fill material. In one embodiment, as in FIG. 1, the pressure source 112 can be a hydraulic actuator that can be computer controlled, but the scope of the invention includes a manually operated syringe loaded with bone fill material, or any other pressurized source of fill material. The source 110 of fill material includes a coupling or fitting 114 for sealably locking to a cooperating fitting 115 at a proximal end or handle 116 of the bone cement injector 105 that has an elongated introducer sleeve indicated at 120. In one embodiment, a syringe-type source 110 can be coupled directly to fitting 115 with a flexible, rigid or bendable (deformable) hydraulic tube 121 that extends to pressure source 112. The fill material then can flow through handle 116 and into a passageway 122 in introducer sleeve 120.

As background, a vertebroplasty procedure using the embodiments disclosed herein can include insertion of the introducer of FIG. 1 through a pedicle of a vertebra for accessing the osteoporotic cancellous bone. The initial aspects of the procedure are similar to a conventional percutaneous vertebroplasty wherein the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician uses a scalpel to make a 1 to 5 mm skin incision over each targeted pedicle. Thereafter, the introducer is advanced through the pedicle into the anterior region of the vertebral body, which typically is the region of greatest compression and fracture. The physician confirms the introducer path posterior to the pedicle, through the pedicle and within the vertebral body by anteroposterior and lateral X-Ray projection fluoroscopic views. The introduction of infill material as described below can be imaged several times, or continuously, during the treatment depending on the imaging method.

Definitions

"Bone fill, fill material, or infill material or composition" includes its ordinary meaning and is defined as any material for infilling a bone that includes an in-situ hardenable material or that can be infused with a hardenable material. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

"Substantially" or "substantial" mean largely but not entirely. For example, substantially may mean about 10% to about 99.999%, about 25% to about 99.999% or about 50% to about 99.999%.

"Osteoplasty" includes its ordinary meaning and means any procedure wherein fill material is delivered into the interior of a bone.

"Vertebroplasty" includes its ordinary meaning and means any procedure wherein fill material is delivered into the interior of a vertebra.

FIGS. 1-5 show that elongated introducer sleeve 120 of bone cement injector 105 with the interior channel or passageway 122 extends about an axis 124, wherein the channel 122 terminates in a distal outlet opening 125. The outlet opening 125 can be a single opening or a plurality of openings disposed about the radially outward surface 128 of the sleeve 120 or an opening at the distal tip 129 of the sleeve. The distal tip 129 can be blunt or sharp. In one embodiment, a core portion 130 (see FIG. 5) of the sleeve 120 is an electrically conductive metal sleeve, such as a stainless steel hypo tube. The core sleeve portion 130 can have both an exterior insulative coating 132 and an interior insulative coating that will be described in greater detail below.

In one embodiment as shown in FIGS. 1-2, the bone fill system 100A has a container or fill material source 110 that is pressurized by a hydraulic source 112 acting on a floating piston 133 (phantom view) in fill material source 110, which can be syringe-like. The introducer sleeve 120 can have a proximal portion 135a that is larger in cross-section than a distal portion 135b, and can have corresponding larger and smaller interior channel portions (e.g., passageway 122) therein. This allows for lesser injection pressures to be used since the cement flow needs to travel less distance through the smallest diameter distal portion of the introducer sleeve 120. The distal portion 135b of the introducer 120 can have a cross section ranging between about 2 mm and 4 mm with a length ranging between about 40 mm and 60 mm. The proximal portion 135a of introducer sleeve 120 can have a cross section ranging between about 5 mm and 15 mm, or between about 6 mm and 12 mm.

As can be seen in the embodiment shown in FIGS. 1-2, the exterior surface of introducer sleeve 120 can carry a sensor system 144 that can sense the flow or movement of a fill material or cement 145 (see FIGS. 3A-3C) proximate to the sensor system 144. The introducer sleeve 120 with such a sensor system 144 is particularly useful in monitoring and preventing extravasation of fill material 145 in a vertebroplasty procedure.

Figure 3A:
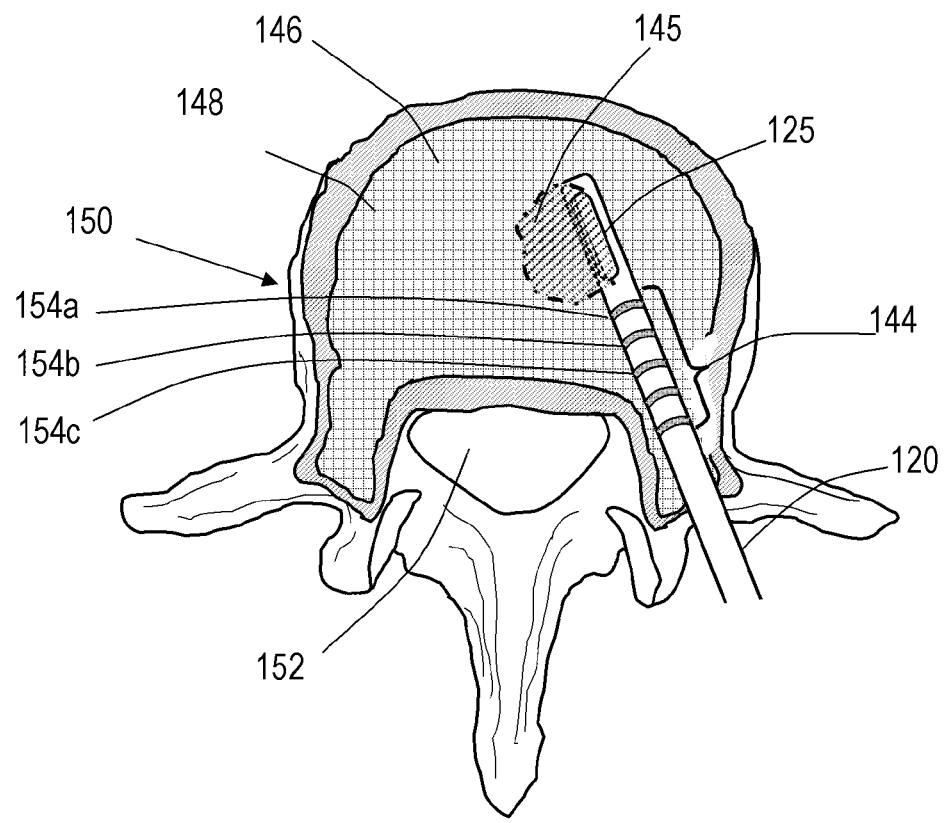
FIG. 3A is a schematic cross-sectional view of a vertebra showing one step in a method according to one embodiment of the invention.
Figure 3B:
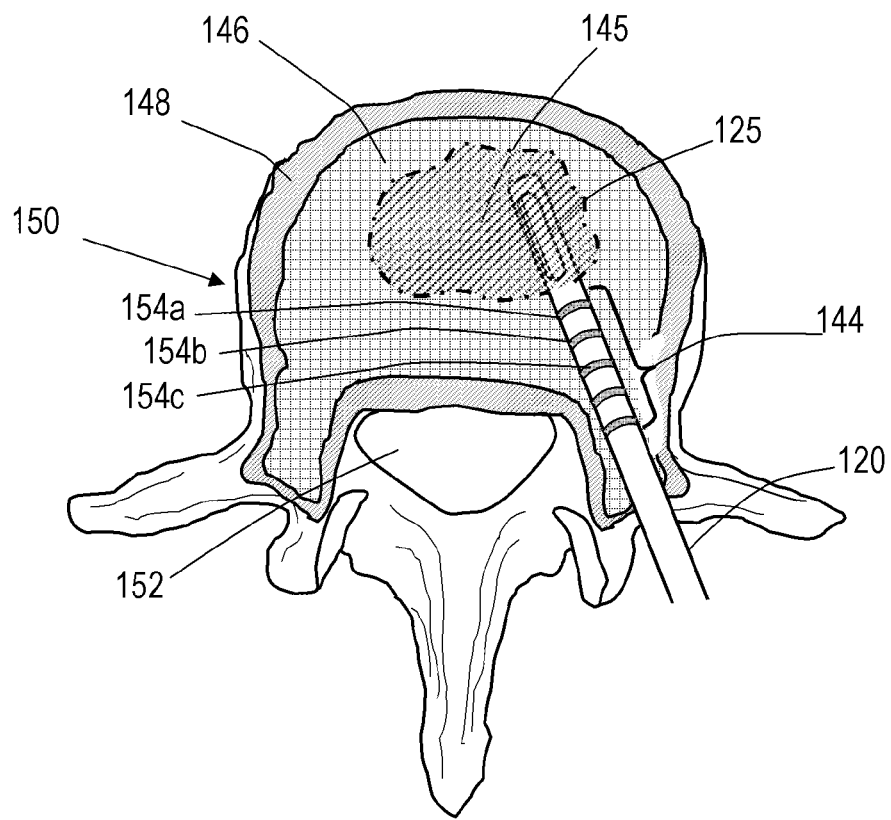
FIG. 3B is a schematic cross-sectional view of the vertebra of FIG. 3A showing a subsequent step in a method for injecting bone cement into a vertebra.
Figure 3C:
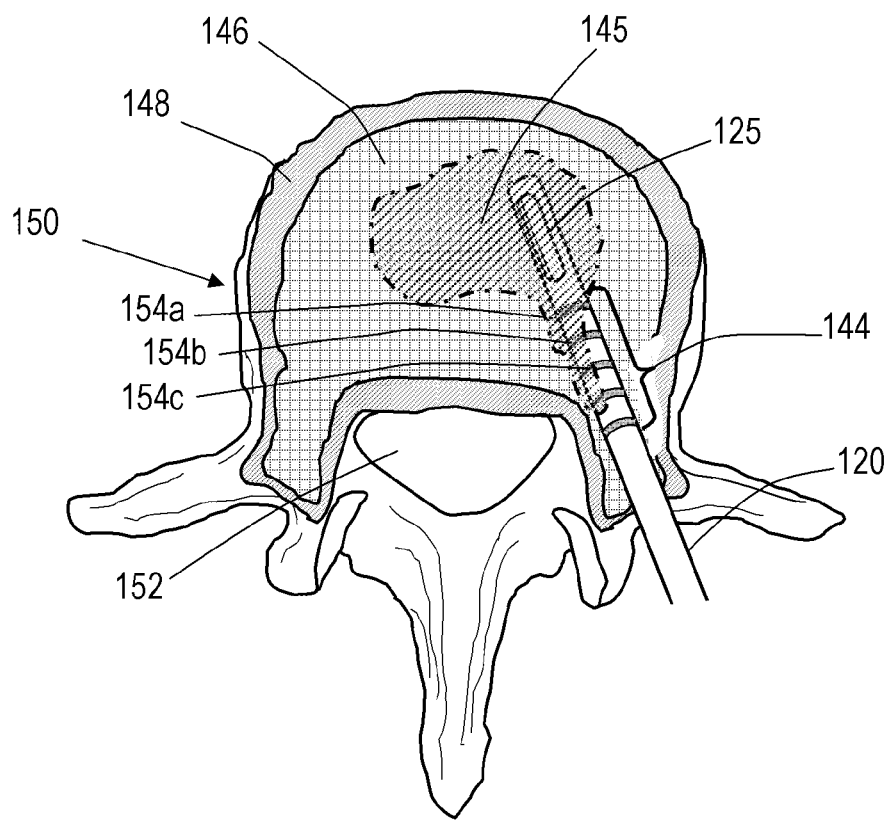
FIG. 3C is a schematic cross-sectional view similar to FIGS. 3A-3B showing a subsequent step in a method of the invention wherein a sensing system detects a retrograde flow.

In one embodiment and method of use, referring to FIGS. 3A-3C, the introducer sleeve 120 is used in a conventional vertebroplasty with a single pedicular access or a bi-pedicular access. The fill material 145 can be a bone cement such as PMMA that is injected into cancellous bone 146 which is within the interior of the cortical bone surface 148 of a vertebra 150.

FIGS. 3A-3B show a progressive flow of cement 145 provided from the outlet 125 of the introducer sleeve 120 into the interior of the vertebra. FIG. 3A illustrates an initial flow volume with FIG. 3B illustrating an increased flow volume of cement 145. FIG. 3C depicts a situation that is known to occur where bone is fractured along the entry path of the introducer 120 and wherein the cement 145 under high injection pressures finds the path of least resistance to be at least partly in a retrograde direction along the surface of introducer 120. The retrograde flow of cement 145 as in FIG. 3C, if allowed to continue, could lead to cement extravasation into the spinal canal 152, which can lead to serious complications. As can be understood from FIG. 3C, the sensor system 144, in one embodiment, can be actuated when cement 145 comes into contact with, or proximate to, the sensor system 144. In one embodiment as shown in FIGS. 2-3C, the sensor system 144 comprises a plurality of spaced apart exposed electrodes or electrode portions (e.g., electrodes 154a, 154b, 154c, etc.) that operate as the sensors 154a-e. Though the illustrated embodiments show that the sensor system 144 includes up to five sensors 154a-e, one of ordinary skill in the art will recognize that the sensor system 144 can include more or fewer sensors. The sensors 154a-c are coupled to a sensor electrical source 155A via a cable 156 and a plug 158a connected to electrical connector 158b in the proximal handle end 116 of the introducer 120 wherein the electrical source 155A can carry a low voltage direct current or Rf current between the opposing potentials of spaced apart electrodes 154a-e. The voltage can be from about 0.1 volt to 500 volts, or from about 1 volt to 5 volts and can create a current path through the tissue between a pair of electrodes 154a-e. The current can be continuous, intermittent and/or multiplexed between different electrode pairs or groups of electrodes 154a-e. The arrangement of electrodes 154a-e can be spaced apart ring-type electrodes and axially spaced apart as shown in FIGS. 1 and 2. In another embodiment, the electrodes can be discrete elements, helically spaced electrodes, or can be miniaturized electrodes as in thermocouples, MEMS devices or any combination thereof. The number of sensors or electrodes can range from about 1 to 100 and can cooperate with a ground pad or other surface portion of the sleeve 120. In one embodiment, the electrodes 154a-e can include a PTC or NTC material (positive temperature coefficient of resistance or negative temperature coefficient of resistance) to thereby function as a thermistor to allow the measurement of temperature, as well as functioning as a sensor. The sensor system 144 can include a controller 155B (FIG. 2) that measures at least one selected parameter of the current flow to determine a change in a parameter (e.g., impedance). When the bone cement 145, which in one embodiment is non-conductive, contacts one or more electrodes 154a-c of the sensor system 144, the controller 155B identifies a change in the selected electrical parameter and generates a signal to the operator. The scope of the invention includes sensor systems capable of sensing a change in electrical properties, reflectance, fluorescence, magnetic properties, chemical properties, mechanical properties or a combination thereof.

Figure 4:
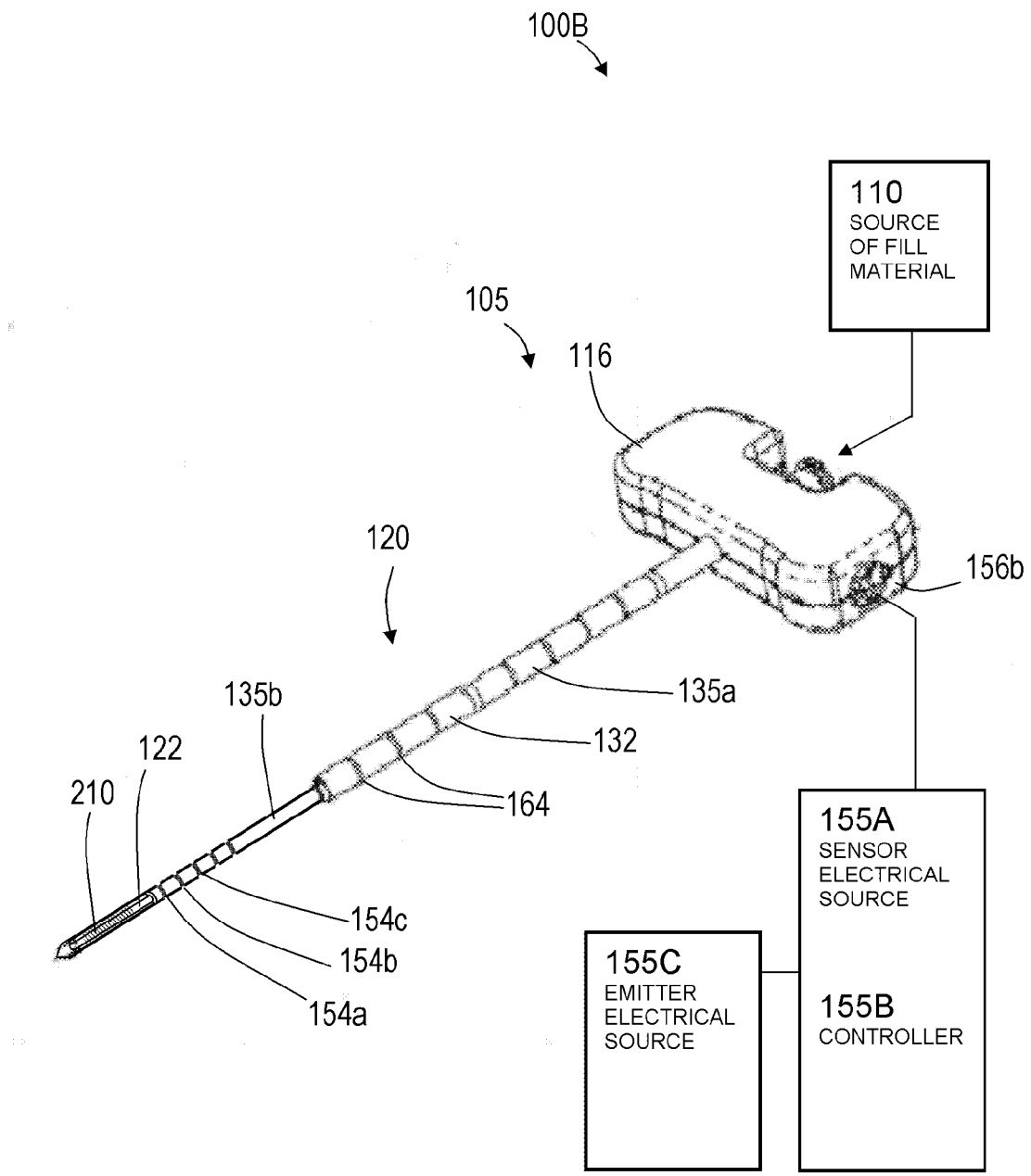
FIG. 4 is a schematic view of another embodiment of a bone cement injector similar to that of FIGS. 1-2.
Figure 5:
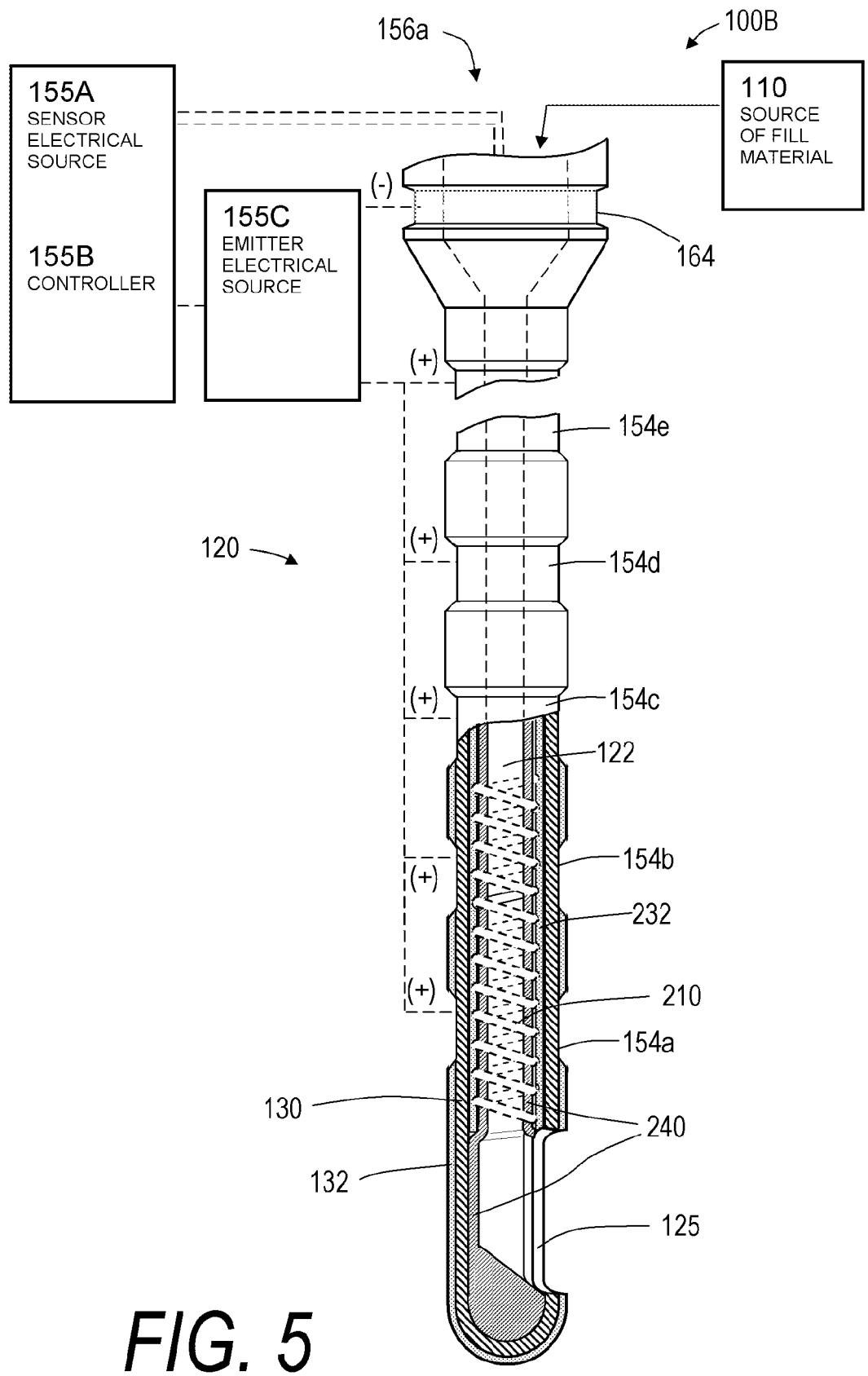
FIG. 5 is a schematic sectional view of a distal portion of the bone cement injector of FIGS. 1-2 with a thermal energy emitter in an interior bore of the injector, a sensor system and scratch-resistant insulative exterior coating.

Now referring to FIGS. 4 and 5, an alternative system 100B includes a bone cement injector 105 that is similar to the injector of FIGS. 1-2, but with a different embodiment of a sensor system together with an additional electrical energy delivery system for applying energy to the fill material 145 for altering its viscosity. In this embodiment, the ring electrode portions (i.e. electrodes 154a, 154b, 154c, etc. in phantom view) are exposed portions of the metal core portion 130 of the sleeve 120 (see FIG. 5) that is coupled via lead 156a to electrical source 155A. The electrode portions 154a, 154b, 154c, etc. can have a first polarity (+) that cooperates with one or more second polarity (−) return electrodes 164 in a more proximal portion of the sleeve 120 coupled by lead 156b to the sensor electrical source 155A. In this embodiment, current flows through the multiple electrode portions 154a, 154b, 154c, etc. and then though engaged tissue to the return electrodes 164, wherein the current flow will signal certain impedance parameters before and during an initial injection of cement 145, as in FIGS. 3A-3B. When there is a retrograde flow of cement 145, as in FIG. 3C, that covers one or more electrode portions 154a, 154b, 154c, etc., then the electrical parameter (e.g., impedance) changes to thus signal the operator that such a retrograde flow has contacted or covered an electrode portion 154a, 154b, 154c, etc. The change in parameter can be a rate of change in impedance, a change in impedance compared to a data library, etc. which will signal the operator of such a retrograde flow. In response to such a signal, the controller 155B also can, in one embodiment, automatically terminate the activation of the pressure source 112.

In the embodiment shown in the system of FIGS. 4 and 5, the bone fill injection system 100B further includes a thermal energy emitter 210 within the interior channel 122 of the introducer 120 (e.g., in the distal section of the introducer 120) for heating a flow of bone cement 145. In one embodiment, the thermal energy emitter 210 is a resistive heating element 210 configured to elevate the temperature of cement 145 to at least 50° C., at least 60° C., at least 70° C., or at least 80° C. The resistive element 210 can be coupled to emitter electrical source 155C, as depicted in FIGS. 4 and 5, together with controller 155B. In one embodiment, the controller 155B can control cement inflow parameters such as variable flow rates, constant flow rates and/or pulsed flows, as well as control the delivery of energy to the bone fill material 145 via the thermal energy emitter 210. The thermal energy delivery is adapted to accelerate polymerization and increase the viscosity of a PMMA or similar bone cement as disclosed in the co-pending U.S. patent applications listed below. In another embodiment, the thermal energy emitter 210 also can be an Rf emitter adapted for ohmically heating a bone cement that carries electrically conductive compositions as disclosed in the below co-pending U.S. patent applications: Ser. No. 11/165,652 filed Jun. 24, 2005; Ser. No. 11/165,651 filed Jun. 24, 2005; Ser. No. 11/208,448 filed Aug. 20, 2005; and Ser. No. 11/209,035 filed Aug. 22, 2005. In another embodiment, the thermal energy emitter 210 can deliver thermal energy to bone cement and can be selected from the group consisting of a resistively heated emitter, a light energy emitter, an inductive heating emitter, an ultrasound source, a microwave emitter and any other electromagnetic energy emitter to cooperate with the bone cement. In the embodiment of FIGS. 4 and 5, the controller 155B can control all parameters of (i) heating the bone cement, (ii) the cement injection pressure and/or flow rate, (iii) energy delivery to cement flows in or proximate the distal end of the introducer and (iv) energy delivery to sense retrograde flows about the exterior surface of the introducer.

In one embodiment depicted in FIG. 5, the resistive heating element 210 comprises a helically wound coil of a resistive material in the interior bore or passageway 122 of the introducer 120. The heating element 210 optionally can be further formed from, or coated with, a positive temperature coefficient material and coupled to a suitable voltage source to provide a constant temperature heater as is known in the art. As can be seen in FIG. 5, the heating element 210 can be disposed within an insulative coating 232 in the interior of the core sleeve 130, which can be a conductive metal as described above.

With continued reference to FIG. 5, the exterior surface of sleeve 120 can have an insulative, scratch-resistant coating indicated at 132 that can comprise a thin layer of an insulative amorphous diamond-like carbon (DLC) or a diamond-like nanocomposite (DCN). It has been found that such coatings have high scratch resistance, as well as lubricious and non-stick characteristics that are useful in bone cement injectors. Such coatings are particularly useful for an introducer sleeve 120 that can carry electrical current for (i) impedance sensing purposes; (ii) for energy delivery to bone fill material 145; and/or (iii) ohmic heating of tissue. For example, when inserting a bone cement injector 105 through the cortical bone surface 148 of a pedicle and then into the interior of a vertebra 150, it is important that the exterior insulative coating portions do not fracture, chip or scratch to thereby insure that the electrical current carrying functions of the injector are not compromised.

The amorphous diamond-like carbon coatings and the diamond-like nanocomposites are available from Bekaert Progressive Composites Corporations, 2455 Ash Street, Vista, Calif. 92081 or its parent company or affiliates. Further information on the coating can be found at: http://www.bekaert.com/bac/Products/Diamond-like%20coatings.htm, the contents of which are incorporated herein by reference. The diamond-like coatings comprise amorphous carbon-based coatings with high hardness and low coefficient of friction. The amorphous carbon coatings exhibit non-stick characteristics and excellent wear resistance. The coatings can be thin, chemically inert and have a very low surface roughness. In one embodiment, the coatings have a thickness ranging between 0.001 mm and 0.010 mm; or between 0.002 mm and 0.005 mm. The diamond-like carbon coatings are a composite of sp2 and sp3 bonded carbon atoms with a hydrogen concentration between 0 and 80%. Another diamond-like nanocomposite coatings (a-C:H/a-Si:O; DLN) is made by Bakaert and is suitable for use in the bone cement injector as described in one embodiment of the invention. The materials and coatings are known by the names Dylyn®Plus, Dylyn®/DLC and Cavidur®.

FIG. 5 further illustrates another aspect of bone cement injector 105 that again relates to the thermal energy emitter (resistive heater 210) within interior passageway 122 of introducer 120. In one embodiment, it has been found that it is advantageous to provide a lubricious surface layer 240 within the interior of resistive heater 210 to ensure uninterrupted cement flow through the thermal emitter 210 without sticking to the passageway 122. In one embodiment, surface layer 240 is a fluorinated polymer such as Teflon® or polytetrafluroethylene (PTFE). Other suitable fluoropolymer resins can be used such as FEP and PFA. Other materials also can be used such as FEP (Fluorinated ethylenepropylene), ECTFE (Ethylenechlorotrifluoroethylene), ETFE, Polyethylene, Polyamide, PVDF, Polyvinyl chloride and silicone. The scope of the invention includes providing a bone cement injector having a flow channel extending therethrough with at least one open termination 125, wherein a surface layer 240 within the flow channel has a static coefficient of friction of less than 0.5, less than 0.2, or less than 0.1.

In another embodiment, the bone cement injector 105 has a flow channel 122 extending therethrough with at least one open termination 125, wherein at least a portion of the surface layer 240 of the flow channel is ultrahydrophobic or hydrophobic which may better prevent a hydrophilic cement from sticking.

In another embodiment, the bone cement injector has a flow channel 122 extending therethrough with at least one open termination 125, wherein at least a portion of the surface layer 240 of the flow channel is hydrophilic for which may prevent a hydrophobic cement from sticking.

In another embodiment, the bone cement injector has a flow channel 122 extending therethrough with at least one open termination in a distal end thereof, wherein the surface layer 240 of the flow channel has high dielectric strength, a low dissipation factor, and/or a high surface resistivity.

In another embodiment, the bone cement injector has a flow channel 122 extending therethrough with at least one open termination 125 in a distal end thereof, wherein the surface layer 240 of the flow channel is oleophobic. In another embodiment, the bone cement injector has a flow channel 122 extending therethrough with at least one open termination 125 in a distal end thereof, wherein the surface layer 240 of the flow channel has a substantially low coefficient of friction polymer or ceramic.

In another embodiment, the bone cement injector has a flow channel 122 extending therethrough with at least one open termination 125 in a distal end thereof, wherein the surface layer 240 of the flow channel has a wetting contact angle greater than 70°, greater than 85°, and greater than 100°.

In another embodiment, the bone cement injector has a flow channel 122 extending therethrough with at least one open termination in a distal end thereof, wherein the surface layer 240 of the flow channel has an adhesive energy of less than 100 dynes/cm, less than 75 dynes/cm, and less than 50 dynes/cm.

The apparatus above also can be configured with any other form of thermal energy emitter that includes the non-stick and/or lubricious surface layer as described above. In one embodiment, the thermal energy emitter can comprise at least in part an electrically conductive polymeric layer. In one such embodiment, the electrically conductive polymeric layer has a positive temperature coefficient of resistance.

Figure 6:
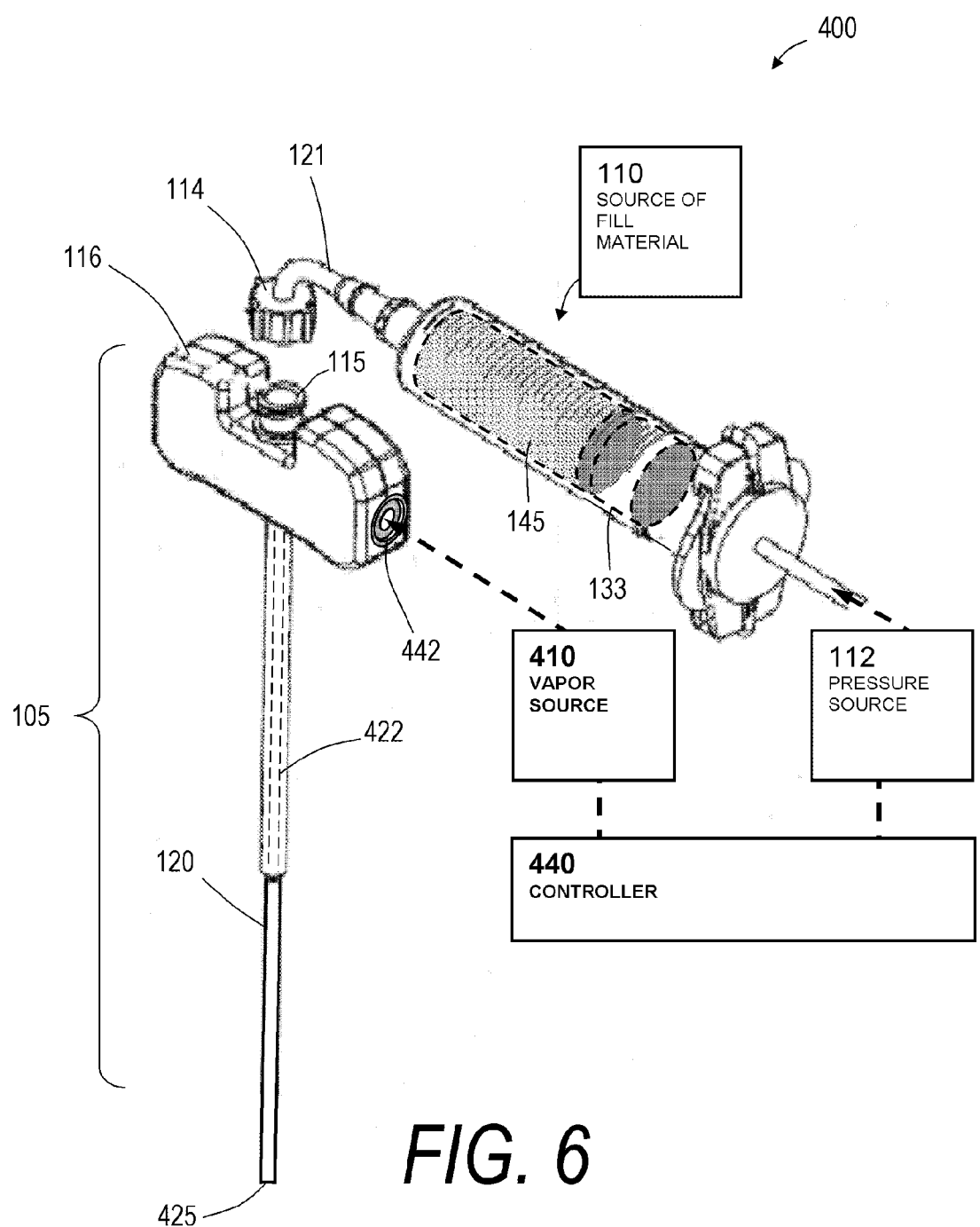
FIG. 6 is a schematic view of another embodiment of a bone cement injector that utilizes a vapor source to apply energy to bone cement.
Figure 7:
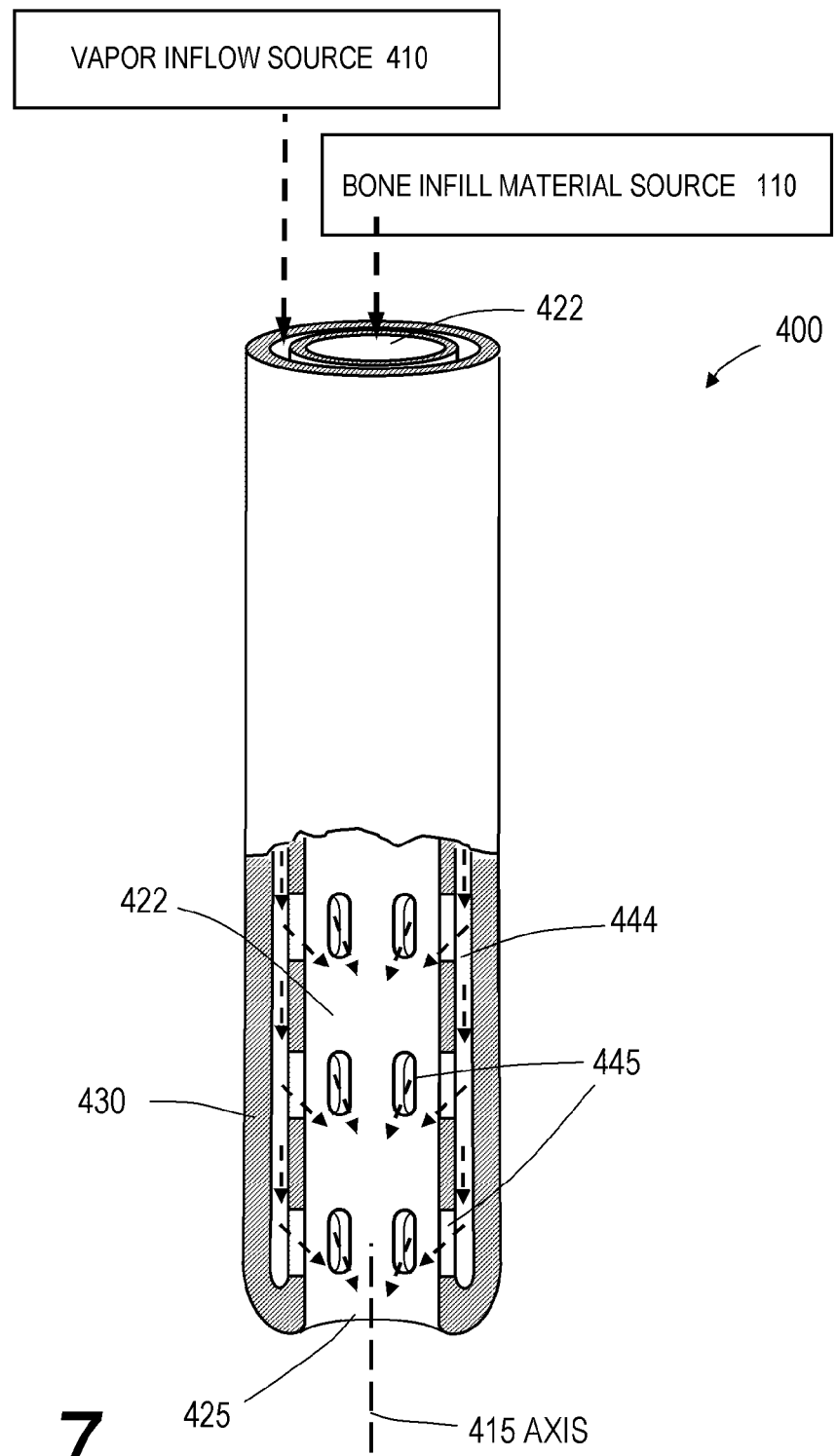
FIG. 7 is a cut-away schematic view of the injector of FIG. 6.

FIG. 6 is an illustration of another embodiment of a treatment system 400 used for introducing bone cement and controlling the viscosity of the cement by applying thermal energy to the cement flow within the injector or introducer 120. In the system of FIGS. 6 and 7, the bone fill injection system 400 introduces a vaporous media from a vapor source 410 into an interior channel or passageway 422 of the introducer 120 for heating a flow of bone cement 145 prior to its ejection from the outlet opening 425 in the distal tip of the introducer 120. In FIG. 6, it can be seen that a controller 440 can control all functional parameters including (i) vapor delivery parameters (e.g., pressure, temperature, vapor quality) from the vapor source 410 for heating the bone cement, and (ii) the cement injection pressure and/or flow rate. The thermal energy delivery from the vapor is adapted to accelerate polymerization and increase the viscosity of a PMMA or similar bone cement as disclosed in the co-pending U.S. patent applications listed below.

Methods and apparatus for generating vapor that may be relevant for the present invention are generally disclosed in U.S. Pat. Nos. 6,911,028, 6,508,816, 6,210,404 and U.S. Application Ser. No. 60/615,900 filed Oct. 5, 2004 titled "Medical Instruments and Techniques for Thermally-Mediated Procedures", Ser. No. 60/643,045 filed Jan. 11, 2005 titled "Surgical Instrument and Method of Use", Ser. No. 11/158,930 filed Jun. 22, 2005 titled "Medical Instruments and Techniques for Treating Pulmonary Disorders", Ser. No. 11/244,329 filed Oct. 5, 2005 titled "Medical Instruments and Methods of Use" and Ser. No. 11/329,381 filed Jan. 10, 2006 titled "Medical Instrument and Method of Use", all of which specifications are incorporated herein by reference.

The source 110 of bone fill material is coupleable to the flow passageway 422, and the vapor source 410 can be sealably coupled to a port 442 in a proximal portion of the injector 105 so as to be in fluid communication with the flow channel 422 for injecting vapor into the flow channel 422. FIG. 7 depicts a sectional view of the introducer 120, which has at least one vapor channel 444, which in one embodiment can be an annulus about the flow channel 422. The vapor channel 444 can include a plurality of vapor outlets 445 that communicate with the flow passageway 422 in the introducer 120. Though FIG. 7 illustrates the vapor channels 444 and plurality of vapor outlet openings 445 in a working end of the introducer 120, the vapor channels 444 and plurality of vapor outlet openings 445 can extend, in one embodiment, along substantially the entire length of the introducer 120. Additionally, the outlet openings 445 can be formed at any desired intervals about the flow passageway 422 (e.g., can be disposed in a spiral configuration about the flow passageway 422 or in a ring configuration about the flow passageway 422). In one embodiment, the vapor channel 444 can extend radially between an outer wall 430 (similar to core portion 130 in FIG. 5) of the introducer 120 and the flow passageway 422. In another embodiment, the at least one vapor channel 444 includes a vapor diffuser structure (not shown) such as a porous or microporous material (e.g., a polymer) that communicates with the flow passageway 422. In another embodiment, the vapor ports or outlets 445 can create a vortex in the flow passageway with angled or other shaped features relative to the axis 415 of the injector.

The controller 440, in one embodiment, can control pressure, flow rates, and material flow intervals in the injector 105 from the source of bone fill material 110. The controller 440 can in one embodiment further control at least one of the pressure, temperature, vapor quality, flow rate, and vapor flow intervals in the injector 105 from the vapor source 410. In one embodiment, the vapor source 410 pulses the vapor flow into the flow passageway 422. The vapor source 410 can be any of the resistive or RF systems described in the patents and patent applications above. For example, a resistive heater can be used to heat a fluid to generate the vapor that is directed to the bone fill material 145 for heating the same.

In another embodiment, the elongated introducer 120 of the bone treatment device can have a distal portion that is flexible, such as one formed from a high-temperature polymer. In another embodiment, the elongated member 120 is deflectable or articulatable.

The device of FIG. 7 depicts one embodiment of the invention where a vapor channel 444 is concentric relative to the cement flow passageway 422. The vapor channel 444 can be singular or plural and also can be non-concentric.

In general, the method of treating bone, comprises advancing a bone cement injector into bone, providing a bone cement flow through the injector, and introducing vapor into the bone cement flow from at least one vapor outlet in the injector. The method utilizes a vapor that has a heat of vaporization of greater that about 60° C., 80° C. and 100° C. The vapor can be generated from at least one of water, saline, Ringer's solution, hypertonic saline and alcohol. The vapor advantageously elevates the temperature of the bone cement flow, thereby altering its viscosity. The method includes the vapor undergoing a phase change upon interaction with the bone cement to deliver energy thereto. The method introduces the vapor from a vapor source 410 remote from the injector, or the vapor can be generated within the injector (e.g., with an energy emitter within the injector 105 that applies heat to a fluid to generate vapor, as discussed above).

In another aspect of the invention, the vapor creates a bone cement emulsion, a foam-like bone cement, or an open-cell bone cement in a cured condition. In one embodiment, the method introduces the vapor to create a vortex in the bone cement.

In another embodiment and method, a flexible or shape memory bone cement injector can be introduced into a curved path in bone, and then cement can be injected from a plurality of ports along the length of the injector working end together with vapor.

The scope of the invention includes, but is not limited to, using additional filler materials such as porous scaffold elements and materials for allowing or accelerating bone ingrowth. In any embodiment, the filler material can comprise reticulated or porous elements of the types disclosed in co-pending U.S. patent application Ser. No. 11/146,891, filed Jun. 7, 2005, titled "Implants and Methods for Treating Bone," which is incorporated herein by reference in its entirety and should be considered a part of this specification. Such fillers also can carry bioactive agents. Additional fillers, or the conductive filler, also can include thermally insulative solid or hollow microspheres of a glass or other material for reducing heat transfer to bone from the exothermic reaction in a typical bone cement component.

The above description of certain preferred embodiments of the invention is intended to be illustrative and not exhaustive. Particular characteristics, features, dimensions and the like that are presented in dependent claims can be combined and fall within the scope of the invention. The invention also encompasses embodiments as if dependent claims were alternatively written in a multiple dependent claim format with reference to other independent claims. Specific characteristics and features as described in certain embodiments of the invention and its method are described in relation to some figures and not in others, and this is for convenience only. While the principles of the invention have been made clear in the exemplary descriptions and combinations, it will be obvious to those skilled in the art that modifications may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

Of course, the foregoing description is that of certain features, aspects and advantages of the present invention, to which various changes and modifications can be made without departing from the spirit and scope of the present invention. Moreover, the bone treatment systems and methods need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or sub-combinations of these specific features and aspects of embodiments may be made and still fall within the scope of the invention. Accordingly, it should be understood that various features and aspects of the disclosed embodiments can be combined with or substituted for one another in order to form varying modes of the discussed bone treatment systems and methods.

What is claimed is:

1. A method of treating bone, comprising:
   providing bone cement injector system with a distal portion positioned in a bone, wherein the distal portion of the injector system comprises an introducer having an interior channel;
   providing a bone cement flow through the injector system; and
   introducing vapor into the bone cement flow from at least one vapor outlet in the interior channel of the introducer of the injector system, wherein the vapor provides thermal energy sufficient to heat the bone cement flow prior to its ejection from the distal portion of the injector system and to accelerate polymerization of the bone cement.

2. The method of claim 1, wherein the vapor has a heat of vaporization of greater that about 60° C.

3. The method of claim 1, wherein the vapor is generated from one or more of water, saline, Ringer's solution, hypertonic saline and alcohol.

4. The method of claim 1, wherein the vapor elevates the temperature of the bone cement flow thereby increasing its viscosity.

5. The method of claim 1, wherein the vapor undergoes a phase change upon interaction with the bone cement.

6. The method of claim 1, wherein introducing the vapor includes ejecting the vapor from a plurality of vapor outlets communicating with a flow passageway in the injector system.

7. The method of claim 1, wherein introducing the vapor is controlled by a controller.

8. The method of claim 1, wherein providing the bone cement flow is controlled by a controller.

9. The method of claim 1, wherein the bone is a vertebra.

10. The method of claim 1, wherein introducing the vapor creates a bone cement emulsion.

11. The method of claim 1, wherein the bone cement comprises at least in part PMMA.

12. A method of treating bone, comprising:
    providing bone cement injector system with a distal portion positioned in a bone, wherein the distal portion of the injector system comprises an introducer having an interior channel;
    providing a bone cement flow through the injector system; and
    introducing vapor into the bone cement flow from at least one vapor outlet in the interior channel of the introducer of the injector system, wherein the vapor heats the bone cement flow prior to its ejection from the distal portion of the injector system, wherein the vapor is adapted to accelerate polymerization of the bone cement, and wherein introducing vapor into the bone cement flow includes introducing vapor via an annular channel in the introducer, the annular channel disposed about the interior channel of the introducer.

13. A method of treating bone, comprising:
    inserting at least a distal portion of an introducer of a bone cement injector system into a bone, wherein the introducer comprises an interior channel;
    delivering a bone cement flow through the interior channel of the introducer into the bone; and
    introducing vapor into the bone cement flow via at least one vapor outlet in the interior channel of the introducer of the injector system, wherein the vapor provides thermal energy sufficient to heat the bone cement flow prior to its ejection from the distal portion of the introducer and to accelerate polymerization of the bone cement.

14. The method of claim 13, wherein the vapor has a heat of vaporization of greater that about 60° C.

15. The method of claim 13, wherein the vapor is generated from one or more of water, saline, Ringer's solution, hypertonic saline and alcohol.

16. The method of claim 13, wherein the vapor elevates the temperature of the bone cement flow thereby increasing its viscosity.

17. The method of claim 13, wherein the vapor undergoes a phase change upon interaction with the bone cement.

18. The method of claim 13, wherein introducing the vapor includes ejecting the vapor from a plurality of vapor outlets communicating with a flow passageway in the injector system.

19. The method of claim 13, wherein introducing the vapor is controlled by a controller.

20. The method of claim 19, wherein the controller controls one or more of vapor pressure, vapor temperature, vapor quality, vapor flow rate, and vapor flow intervals.

21. The method of claim 13, wherein delivering a bone cement flow is controlled by a controller.

22. The method of claim 21, wherein the controller controls one or more of bone cement flow pressure, bone cement flow rates, and bone cement flow intervals.

23. The method of claim 13, wherein the bone is a vertebra.

24. The method of claim 13, wherein introducing the vapor creates a bone cement emulsion.

25. The method of claim 13, wherein the bone cement comprises at least in part PMMA.

* * * * *